United States Patent [19]

Schneider

[11] 4,423,036

[45] Dec. 27, 1983

[54] ACID SOLUBLE PLATELET AGGREGATING MATERIAL ISOLATED FROM HUMAN UMBILICAL CORD

[75] Inventor: Morris D. Schneider, Knoxville, Tenn.

[73] Assignee: Research Corporation, Knoxville, Tenn.

[21] Appl. No.: 289,154

[22] Filed: Aug. 3, 1981

[51] Int. Cl.³ .......................... A61K 35/48; C01N 1/00
[52] U.S. Cl. ........................................ 424/105; 436/69
[58] Field of Search ............................ 424/105; 436/69

[56] References Cited

U.S. PATENT DOCUMENTS 3,910,822  10/1975  Pentchev et al. .................. 424/105
4,217,339   8/1980  Bohn et al. ........................ 424/105

*Primary Examiner*—Sam Rosen
*Attorney, Agent, or Firm*—Scully, Scott, Murphy & Presser

[57] ABSTRACT

Acid soluble, pepsin sensitive platelet aggregating material isolated from human umbilical cord tissue by extraction with dilute aqueous acid, method of isolation and use to control bleeding.

14 Claims, 2 Drawing Figures

```
          Repeated homogenization.  Kept overnight (4°C).
              Repeated centrifugation.
                       |
                       |
                       |                    Aqueous phase, Fraction 3,
                       |                    pH 3.3.  Filtered through
                       |                    gause (125 ml).  Placed in
     Pelleted tissue   ↓                    telescoped Visking sac.  Dia-
       remaining  ← — — — — →               lysed as described above.
          |
          ↓
   + 100 ml of 83.5 mM
   glacial acetic acid
          |
          |
          |
          ↓
  Repeated homogenization.  Kept overnight (4°C).
       Repeated centrifugation.
                       |
                       |
                       |                    Aqueous phase, Fraction 4,
                       |                    pH 3.28.  Filtered through
                       |                    gauze (125 ml).  Placed in
     Pelleted tissue   ↓                    telescoped Visking sac.  Dia-
       discarded.  ← — — — — →              lyzed as described above.

Dialysis continued for 5-7 days with
            daily changes of 4 l of 16.7 mM
            glacial acetic acid.
                       |
                       |
                       ↓
```

Small aliquots (1-2 ml) of retentates sampled for monitoring
platelet aggregating activity.  Fractions 2-4 invariably contain
the highest levels of the potent platelet pro-aggregating material.
Three retentates are pooled and again blended in macrohomogenizer.
Blended cord extractables are then subjected to ultracentrifugation
(105,000 xg for 60 min. at 0°C).
                       |
                       |
                       ↓
         Suspension separates into 3 phases.

(1) A crystal clear supernatant, Phase 1.
This is entirely free of platelet aggregating material
and is discarded.

(2) A gelled precipitate, Phase 2.
This is an opalescent viscous material that
contains high levels of the potent aggregating material.

(3) A pelleted component, Phase 3.
This is composed of the remaining insoluble
cord tissue and is discarded.

FIG. IB

ACID SOLUBLE PLATELET AGGREGATING MATERIAL ISOLATED FROM HUMAN UMBILICAL CORD

This invention was made in the course of, or under a contract with the United States Department of Energy.

BACKGROUND OF THE INVENTION

Platelet aggregation is of a primary importance in the clotting mechanism of blood. Materials that stimulate platelet action also promote blood clotting and are called hemostatic agents. In the prior art, it has been suspected that certain components of the arterial wall are related to platelet action. The function of the particular components, either singly or in combination, has not been well understood. The study of platelet aggregation is useful for determining the role of platelets in a variety of hemostatic diseases, and in diagnostic tests for detecting the presence of diseases characterized by abnormal platelet function or activity. A potent, highly sensitive platelet aggregating agent has long been needed.

It is an object of this invention to provide a hemostatic agent which is highly effective for promoting platelet aggregation and blood clotting.

It is a further object to provide an agent useful for studying platelet function and detecting functional disorders in the platelet aggregating mechanism.

It is a further object to provide a method for producing a highly potent hemostatic agent from human umbilical cord tissue.

It is a further object to provide a method for clotting blood and for controlling bleeding from a wound or incision.

It is a further object of this invention to provide a vasoconstrictive agent.

SUMMARY OF THE INVENTION

These and other objects have been achieved by providing acid soluble platelet aggregating compositions isolated from human umbilical cord tissue. It has been discovered that the compositions of this invention will stimulate platelet aggregation when an effective amount of it contacts a platelet containing suspension such as platelet rich plasma or whole blood either in vitro or in vivo. The compositions therefore are useful in methods for controlling external bleeding from a wound or incision by contacting the wound or incision with an effective amount of the selected composition either alone or with a suitable carrier. The invention also comprises a method of detecting abnormal platelet function comprising contacting a solution containing platelets suspected of abnormal function, such as plasma or whole blood, with a composition of the invention and comparing the aggregation response of the plasma or whole blood under study to the response of normal platelets.

The human fetal umbilical cord is a flexible ropelike structure. In the living organism, it links the fetal umbilicus with the maternal placenta, supporting two important umbilical arteries and a single umbilical vein. In the newborn, the umbilical cord measures 50 to 60 cm in length by 1 cm in diameter. It consists largely of a soft, pulpy, loose connective tissue known as Wharton's jelly. This loose matrix cord material that shows a swelling behavior contains high molecular weight acid mucopolysaccharides. Hyaluronic acid is a principal polysaccharide. The umbilical cord also contains a substantial amount of a loose connective tissue characterized by a network of utlrafine, interlacing collagen fibrils that increase in quantity with age of the developing fetus. Stellate fibroblasts can be seen microscopically throughout Wharton's jelly. The fibroblast processes often seem to fuse with neighboring cells.

BRIEF DESCRIPTION OF THE DRAWINGS

FIGS. 1A and 1B taken together show the scheme of a procedure for preparing the hemostatic composition of the invention.

DETAILED DESCRIPTION

Figure 1A:
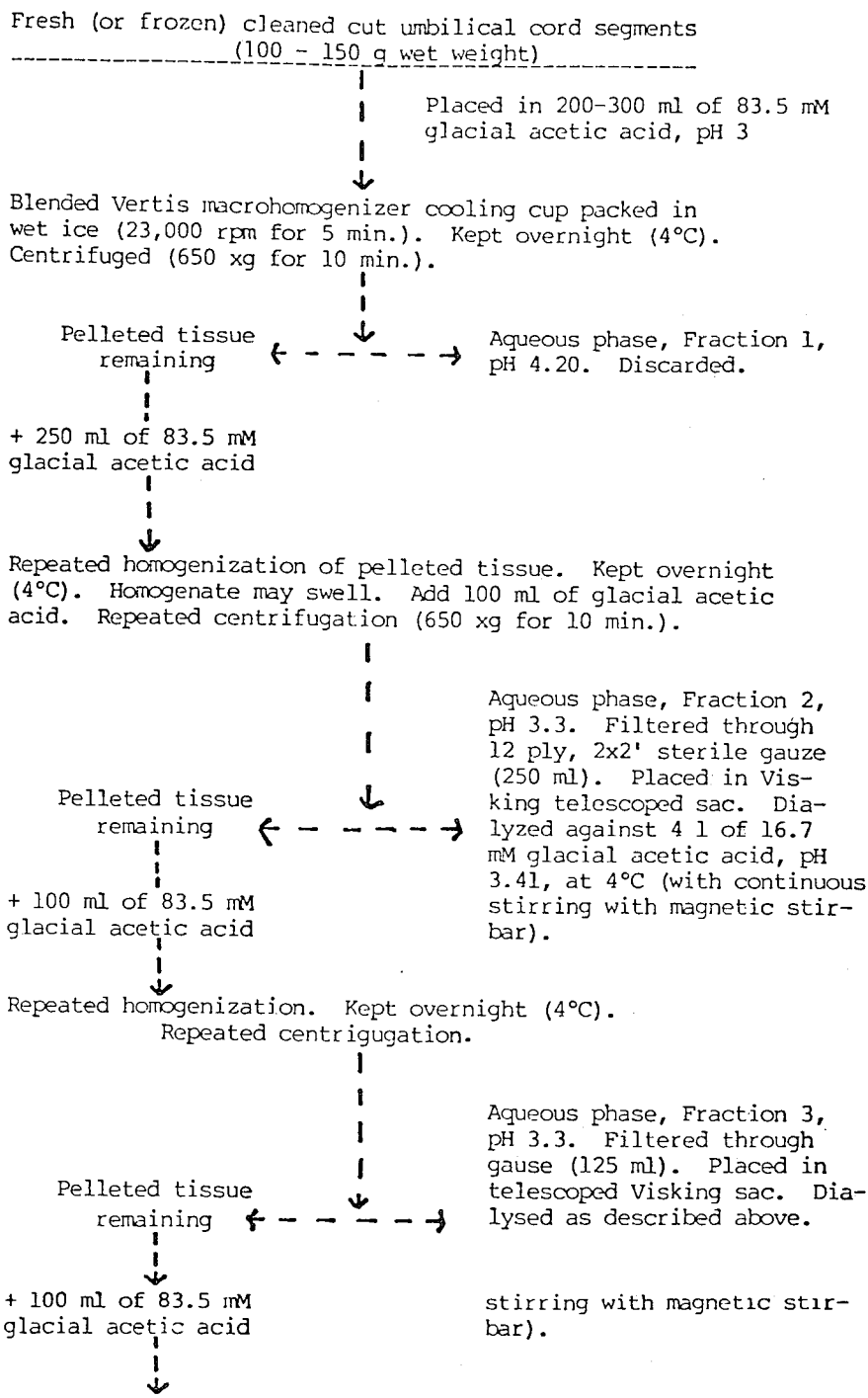

A principal aspect of this invention is the discovery that human umbilical cord contains an acid soluble material which is highly potent for stimulating the aggregation of platelets of mammals, including humans.

In the first step of this invention, segments of human umbilical cord tissue cleaned of all loose connective tissue, adventitial layer, blood cellular fragments, platelets, plasma, etc. by extensive rinsing, is extracted with acid.

In the presently preferred procedure for preparing the cord tissue to undergo the isolation procedure of this invention, the tissue is cut into small segments (approximately 5×5 mm) and thorougly cleansed by washing or rinsing with an appropriate wash liquid. Any of a variety of physiologically safe liquids including water, but preferably balanced salt solutions can be used for cleansing. Physiological saline is useful. Tyrode's solution which is a balanced salt solution simulating the salt content of mammalian body fluids and including glucose, sodium bicarbonate and magnesium salts stabilized at a pH of about 7.4 is preferred. Other balanced salt solutions such as Hank's or Earle's can also be employed.

The cleansed segments may be utilized immediately, but will normally be prepared in relatively large amounts and stored at $-20°$ C. to $-85°$ C. until realy for use.

One procedure for preparing the hemostatic composition of this invention is outlined in the scheme shown on FIGS. 1A and 1B.

The extraction and homogentation temperature is from about $0°$ C. to about $5°$ C. Dialysis is effected in the same temperature range.

Water soluble organic and inorganic acids in dilute solution may be employed for the extraction procedure. The concentration of acid will typically be from about 0.05 molar to about 0.1 molar. It is preferred to use the same acid for dialysis as for extraction, but at a somewhat higher concentration. Lower organic monocarboxylic acids, especially acetic acid are preferred.

Treatment of the retentate at any of the dialysis steps with pepsin destroys the ability of the remaining material to function as a platelet aggregating material. The products of the invention are, therefore, pepsin sensitive.

In the first step of the outlined procedure for obtaining the valuable hemostatic agent of this invention, cleansed umbilical cord segments are homogenized in an aqueous medium, retained for 8 to 20 hours at about $4°$ C. and separated by centrifugation. The aqueous phase, Fraction 1, is discarded, and the pellet taken up in an aqueous medium and homogenized. The mixture is let stand for 8 to 20 hours to effect an extraction of at least a part of the hemostatic agent, and again centrifuged. The resulting aqueous phase, Fraction 2, is useful to effect blood clotting.

The pellet remaining after centrifugation is again homogenized, extracted and centrifuged. The centrifugate, Fraction 3, is also active to effect blood clotting.

The procedure is repeated to obtain Fraction 4 which is also active.

Fractions 2-4, either separately or combined, are dialyzed for 5 to 7 days. The retentate which is also active is ultracentrifuged to form a suspension of three phases as shown in the outline. A highly purified hemostatic agent is obtained as Phase 2 of the centrifugate.

Highly purified samples of the hemostatic agent can be obtained by continuous dialysis. For example, the gelled cord precipitate from combined Fractions 2, 3 and 4, may be blended in a macrohomogenizer and dialyzed, for example, in a Visking sac against 4 l of 16.7 mM glacial acetic acid for 5 to 7 days at 4° C. with continuous stirring with a magnetic bar. The resulting highly purified cord concentrate may be frozen, for example, at −85° C. and stored until ready for use.

Alternatively, the highly purified retentate from the above described dialysis may be subjected to ultracentrifugation, for example, at 105,000 xg for 1 hour at 0° C. to separate it into three fractions, a clear supernatant and a pellet, both of which are substantially free of aggregating activity and a middle gelled fraction which is analogous to the original gelled fraction and is an opalescent, viscous material containing substantially all of the aggregating activity.

As with many products isolated from natural sources, particularly animal sources, the exact analysis and properties of each isolated product will vary. The composition of this invention is, however, readily identified by its platelet aggregating activity, its hypertensive activity and of course, its source and method of isolation. The actual analysis of product may vary from one individual to the next, or with slightly different methods of isolation.

The micro-Kjeldahl protein assay method has been used to determine the absolute amount of protein normally present in the acid soluble, pepsin sensitive products of this invention. The results are shown below.

TABLE 1

| Chemical Composition Of Human Fetal Umbilical Cord Concentrate | | | |
|---|---|---|---|
| Starting Cord Tissue (in grams of wet weight) | Fraction Isolated (Phase 2) | Yield Dry Weight (mg) | Micro-Kjeldahl Assay (% Nitrogen per mg of dry weight) |
| Preparation 1 100 | 2 | 225[b] | 18.4[b,c] |
|  | 3 | 240 | 16.1 |
| Preparation 2 150 | (2 + 3 + 4)[a] | 305 | 18.8 |
| Standards | | | |
| Bovine Serum albumin (50 mg) | — | — | 14.2 |
| Ammonium sulfate (50 mg) | — | — | 22.0 |

[a]Three fractions were combined to produce a single Phase 2 fetal cord concentrate.
[b]Analytic data are the means of duplicate determinations.
[c]To convert to % protein, multiply % N by 6.25.

To determine dry weight, replicate samples (1–3 ml aliquots) of microhomogenized product were placed in dry tare weighed aluminum foil dishes. The samples were dispersed in the dishes by adding 2 ml of absolute ethanol and were then dried to constant weight in an air convection oven at 70° C. for 24 hours.

Amino acid composition was determined by a JEOL-JCL-6AH analyzer available from Japan Electron Optics Laboratory using a one column analyzer. The following table gives the data on amino acid composition of hydrolysates of typical products of the invention expressed as residues per 1,000 total amino acid residues.

TABLE 2

| AMINO ACID | BURRO A30 | AMINO ACID | BURRO A30 |
|---|---|---|---|
| Lysine | 30.1 | Glycine | 257.8 |
| Histidine | 14.4 | Alanine | 111.9 |
| Hydroxylysine | 6.4 | Cysteine | 6.3 |
| Arginine | 64.2 | Valine | 41.2 |
| Hydroxyproline | 36.1 | Methionine | 8.1 |
| Aspartic acid | 51.3 | Isoleucine | 18.9 |
| Threonine | 19.6 | Leucine | 41.1 |
| Serine | 38.6 | Tryosine | 7.8 |
| Glutamic acid | 90.3 | Phenylalanine | 20.1 |
| Proline | 100.8 | | |

The products were analyzed by SDS-PAGE analysis. Sodium dodecyl sulfate complexes were prepared to give a final protein concentration of 1 mg/ml in Trisborate cathode buffer (pH 8.64) containing SDS (3 mg/ml), 2.5% mercaptoethanol, and 6% sucrose. After a twenty minute incubation period (22° C.), the mixtures were treated at 100° C. for five minutes and stored at −20° C. until ready for analysis.

Electrophoresis at 1 to 1.5 MA/Tube was by buffer system J4179 (Jovin et al. Multiphasic Buffer System Output, Federal Scientific and Technical Information, U.S. Department of Commerce, PB 196085-196091, Springfield, Va., 1971) with SDS in the cathode buffer using a T=1.9%, C=9.4% stacking gel containing 20% sucrose, and with T=5.0%, C=3.2% separating gel. The gels were strained with Coomassie brilliant blue. Molecular weights were estimated from a standard curve $\log_{10}$ molecular weight versus relative mobility with respect to the leading edge of the buffer front.

When so analyzed, the products of this invention show bands characteristic of the following molecular weights;

| | |
|---|---|
| 300,000 | 200,000 |
| 250,000 | 132,000 |
| 220,000 | 116,000 |

To establish the platelet aggregating activity of the products of this invention, it was necessary to prepare protein rich plasma (PRP) and protein poor plasma (PPP) from selected subjects. Human subjects, when selected, were not permitted to ingest aspirin or any other medication for ten days prior to testing. Whole blood was drawn from a juglar (animal) or forearm (human) vein through a disposable sterile silicone-treated needle, using a sterile plastic (35 ml) syringe previously wetted with a filter sterilized anticoagulant of 3.8% trisodium citrate dihydrate and 0.5% dextrose in triple distilled water (pH 7.0). Collections of blood were immediately admixed with 0.1 volume of the anticoagulant in capped polystyrene tubes to avoid glass activation of platelets and plasma. Differential slow centrifugation at 22° C. was used to prepare citrated PRP—animal or human blood was centrifuged twice (when necessary) sequentially at 95G for 30 minutes and the two fractions were cooled. The PRP was collected with a disposable polyethylene blub pipet. To prevent pH change and optimize the platelet function during tests, the PRP was stored at 22° C. in capped plastic tubes. PPP was obtained by centrifugation of the remaining blood at 650G for 20 minutes. Platelet counts in the PRP were determined by phase contrast microscopy using 1% ammonium oxalate.

The products of this invention are useful for effecting platelet aggregation in humans and farm animals when utilized alone or with a pharmaceutically acceptable carrier.

The products of this invention were studied to determine their ability to cause platelet aggregation in humans and farm animals by the in vitro turbidimetric (optical density) technique as described by G. V. R. Born (Nature 194:927–929, 1962). Platelet responsiveness was monitored by this technique in which 0.05 ml of the umbilical cord concentrate was added to 0.45 ml of citrated platelet-rich plasma (PRP) at 37° C. The changes in light transmission due to aggregation of the platelets in the PRP were continuously recorded on a strip-chart recorder by a sensitive, self-calibrating aggregometer (Platelet Aggregation Profiler, Model PAP-2, Bio/Data Corporation, Willow Grove, Pa.). In these experiments, fresh whole blood obtained by venipuncture from healthy goats and healthy human volunteers was collected into 0.1 volume of 0.13 M sodium citrate (anticoagulant) solution plus 500 mg % of glucose, pH adjusted to 7.2. PRP was prepared by low speed centrifugation (95 xg for 30 min.) and kept at 22° C. Testing with human PRP was done within 2-3 hr. of blood collection. Goat PRP remained stable for several hours longer at 22° C.

Three parameters of platelet aggregation were measured:

(a) Delay or lag time to the initiation of the platelet aggregation (in seconds).

(b) Intensity of the platelet aggregation (the percent aggregation response corresponding to percent light transmission).

(c) Rate or velocity of the platelet aggregation as calcined from the steepest slope of the optical transmission trace on the recording paper, i.e., [(slope/second)×100].

The aggregation responsiveness was monitored down to the lowest concentration of the cord concentrate (in micrograms or nanograms as dry weight) in 0.05 ml of 16.7 mM glacial acetic acid which demonstrated a measurable response in the PRP.

The results are shown in Table 3. These were determined from the data tracings produced by the Platelet Aggregation Profiler over the entire range of amounts of the fetal cord concentrate of the invention in micrograms and nanograms dry weight added to 0.45 ml of goat or human platelet richplasma.

TABLE 3

Platelet Pro-aggregatory Agent(s) Present in Human Fetal Umbilical Cord Concentrate

| Amount (dry weight) of cord concentrate contained in 0.05 ml of diluent[a] added to 0.45 ml of PRP | Delay time to onset of platelet aggregation (sec) | | | | Maximal decrease in optical density of PRP (% aggregation) | | | Maximal velocity of aggregation [(slope/sec)] × 100 | | |
|---|---|---|---|---|---|---|---|---|---|---|
| | Goat PRP | Human PRP | | Human PRP(3)[b] | Goat PRP | Human PRP | Human PRP | Goat PRP | Human PRP | Human PRP |
| 122 μg | 6 | 5 | 125 μg | 5 | 100 | 98 | 96 | 300 | 300 | 181 |
| 61 μg | 6 | 5 | 62.5 μg | 7 | 96 | 96 | 94 | 300 | 300 | 198 |
| 24.4 μg | 7 | 7 | 31.3 μg | 11 | 100 | 94 | 91 | 300 | 300 | 208 |
| 12.2 μg | 8 | 7 | 15.6 μg | 12 | 100 | 100 | 94 | 300 | 225 | 189 |
| 6.1 μg | 12 | 7 | 7.8 μg | 12 | 100 | 96 | 88 | 174 | 219 | 181 |
| 3.05 μg | 17 | 10 | 3.9 μg | 17 | 100 | 100 | 91 | 167 | 225 | 174 |
| 1.53 μg | 22 | 12 | 1.95 μg | 22 | 89 | 94 | 85 | 146 | 208 | 167 |
| 760 ng | 22 | 18 | 980 ng | 19 | 82 | 96 | 92 | 139 | 185 | 219 |
| 380 ng | 24 | 22 | 490 ng | 23 | 89 | 94 | 92 | 149 | 203 | 209 |
| 190 ng | 30 | 24 | 245 ng | 24 | 88 | 87 | 83 | 119 | 189 | 174 |
| 95 ng | 34 | 34 | 60 ng | 26 | 80 | 40 | 88 | 102 | 77 | 149 |
| 48 ng | 36 | 38 | 30 ng | 28 | 64 | 30 | 82 | 82 | 58 | 146 |
| 24 ng | 67 | 0 | 15 ng | 43 | 29 | 0 | 26 | 22 | 0 | 60 |

[a]16.7 mM glacial acetic acid, pH 3.41.
[b]Mixed platelets in a pool of PRP from 3 human donors.

From an analysis of the results reported in Table 3, it can be seen that:

(1) The lag time to the onset of the platelet aggregation lengthens with decreasing amounts of cord concentrate added.

(2) The % aggregation continues high to additions as low as 50 nanograms of cord concentrate added.

(3) The aggregation velocity is extremely high.

One use of acid soluble, pepsin sensitive, non-dialyzable, proteinaceous composition of this invention is as a diagnostic tool to provide information about platelet function in human and other warm-blooded species, e.g. mammals. It appears that platelets are more sensitive to this material than to any known commercial product or arterial collagen of other species. By contacting a solution containing platelets (e.g. plasma, or whole blood) with a composition of this invention and comparing the aggregation response to that of normal patients, platelet dysfunctions or hemostatic disorders can be detected. Platelet dysfunction is characteristic of several diseases. Some drugs such as aspirin have been shown to affect platelet activity. Minor differences in platelet activity can be detected by the response to the composition of this invention, thus indicating the course of treatment, e.g. avoidance of the drug. The compositions of the invention are highly sensitive for detecting hyperactive platelets such as are associated with coronary heart disease, myocardial ischemia, and myocardial infarction. In addition, the extractable collagenous material of this invention is a valuable research tool for studying the role of platelet activity in such diseases as arteriosclerosis, heart attack, stroke, pulmonary embolism, drug toxicity and ingestion of toxic metal pollutants such as cadmium.

Another utility for the fibrillar collagen of this invention is to stimulate the clotting of the blood in wounds or surgical incisions including skin grafts. The composition is useful for internal applications, such as for controlling hemorrhaging from ruptured organs during veterinary surgery. For this use, the material should be in a pharmaceutically acceptable carrier, e.g. water, Hank's, Earle's, Tyrode's solution or other balanced salt solution. Alternatively, the active material can be separated from solution, i.e. by freeze-drying and applied as a sponge or powder.

On the basis of the amino acid analysis given above, particularly the molar ratios of PRO/HO-PRO, LYS/HO-LYS, HO-PRO-TYR, GLY/VAL and PRO/GLY, it appears that a major constituent of the composition of this invention most closely resembles a type 1 collagen. However, the material is present at a high concentration and is therefore useful for purposes for which no known natural collagen can be employed, for example, rapid platelet aggregation or control of bleeding.

While it is not understood just how the collagen of umbilical cord tissue functions in its natural environment, it is clear that it functions differently from the compositions of this invention. The platelet aggregating action of these compositions, even for autologous platelets, is so greatly accelerated over previously known compositions of this type that the action might almost be considered explosive.

Internal injection in a guinea pig of the highest dilution of a hemostatic agent of this invention still demonstrating platelet aggregating properties will produce a dramatic rise in blood pressure, accompanied by extensive thrombus formation and acute heart attack. The rapid rise in blood pressue illustrates the vasoconstrictor action of the products, and this enhances their utility for controlling bleeding.

What is claimed is:

1. An acid soluble, pepsin sensitive non-dialyzable, proteinaceous hemostatic agent isolated from human umbilical cord tissue characterized by the ability to enhance platelet aggregating activity in mammalian blood, stable for extended period of time at temperatures as low as −85° C., containing the following average number of amino acid residues per 1,000 total amino acid residues:

| Lysine | 30.1 | Glycine | 287.8 |
|---|---|---|---|
| Histidine | 14.4 | Alanine | 111.9 |
| Hydroxylysine | 6.4 | Cysteine | 6.3 |
| Hydroxyproline | 36.1 | Valine | 41.2 |
| Aspartic Acid | 51.3 | Methionine | 8.1 |
| Threonine | 19.6 | Isoleucine | 18.9 |
| Serine | 38.6 | Leucine | 41.1 |
| Glutamic Acid | 90.3 | Tryosine | 7.8 |
| Proline | 100.8 | Phenylalanine | 20.1 |
| Arginine | 69.2 | | | which on SDS-PAGE electrophoresis produces bands characteristic of the following molecular weights:

| 300,000 | 200,000 |
|---|---|
| 250,000 | 132,000 |
| 220,000 | 116,000 |

2. A hemostatic agent of claim 1 in a pharmaceutically acceptable carrier.

3. A hemostatic agent of claim 1 in an externally administerable pharmaceutical carrier.

4. A hemostatic agent of claim 1 in a balanced salt solution.

5. A hemostatic agent of claim 1 in water.

6. A method of stimulating platelet aggregation in mammalian plasma or whole blood which comprises contacting said plasma or whole blood with an amount which is effective to stimulate platelet aggregation of acid soluble, pepsin sensitive, non-dialyzable, proteinaceous hemostatic agent isolated from human umbilical cord tissue characterized by the ability to enhance platelet aggregating activity in mammalian blood, stable for extended periods of time at temperatures as low as −85° C., containing the following average number of amino acid residues per 1,000 total amino acid residues:

| Lysine | 30.1 | Glycine | 287.8 |
|---|---|---|---|
| Histidine | 14.4 | Alanine | 111.9 |
| Hydroxylysine | 6.4 | Cysteine | 6.3 |
| Hydroxyproline | 36.1 | Valine | 41.2 |
| Aspartic Acid | 51.3 | Methionine | 8.1 |
| Threonine | 19.6 | Isoleucine | 18.9 |
| Serine | 38.6 | Leucine | 41.1 |
| Glutamic Acid | 90.3 | Tryosine | 7.8 |
| Proline | 100.8 | Phenylalanine | 20.1 |
| Arginine | 69.2 | | | which on SDS-PAGE electrophoresis produces bands characteristic of the following molecular weights:

| 300,000 | 200,000 |
|---|---|
| 250,000 | 132,000 |
| 220,000 | 116,000 |

7. A method as in claim 6 wherein the hemostatic agent is in a pharmaceutically acceptable carrier.

8. A method of controlling external bleeding from a wound or incision comprising contacting said wound or incision with an amount which is effective to control bleeding of an acid soluble, pepsin sensitive, non-dialyzable, proteinaceous hemostatic agent isolated from human umbilical cord tissue characterized by the ability to enhance platelet aggregating activity in mammalian blood, stable for extended periods of time at temperatures as low as −85° C., containing the following average number of amino acid residues per 1,000 total amino acid residues:

| Lysine | 30.1 | Glycine | 257.8 |
|---|---|---|---|
| Histidine | 14.4 | Alanine | 111.9 |
| Hydroxylysine | 6.4 | Cysteine | 6.3 |
| Hydroxyproline | 36.1 | Valine | 41.2 |
| Aspartic Acid | 51.3 | Methionine | 8.1 |
| Threonine | 19.6 | Isoleucine | 18.9 |
| Serine | 38.6 | Leucine | 41.1 |
| Glutamic Acid | 90.3 | Tryosine | 7.8 |
| Proline | 100.8 | Phenylalanine | 20.1 |

-continued

| | |
|---|---|
| Arginine | 69.2 | which on SDS-PAGE electrophoresis produces bands characteristic of the following molecular weights:

| | |
|---|---|
| 300,000 | 200,000 |
| 250,000 | 132,000 |
| 220,000 | 116,000 |

9. A method of detecting abnormal platelet function comprising contacting platelets in plasma or whole blood under test with an acid soluble, pepsin sensitive, non-dialyzable, proteinaceous hemostatic agent isolated from human umbilical cord tissue characterized by the ability to enhance platelet aggregating activity in mammalian blood, stable for extended periods of time at temperatures as low as $-85°$ C., containing the following average number of amino acid residues per 1,000 total amino residues:

| | | | |
|---|---|---|---|
| Lysine | 30.1 | Glycine | 287.8 |
| Histidine | 14.4 | Alanine | 111.9 |
| Hydroxylysine | 6.4 | Cysteine | 6.3 |
| Hydroxyproline | 36.1 | Valine | 41.2 |
| Aspartic Acid | 51.3 | Methionine | 8.1 |
| Threonine | 19.6 | Isoleucine | 18.9 |
| Serine | 38.6 | Leucine | 41.1 |
| Glutamic Acid | 90.3 | Tryosine | 7.8 |
| Proline | 100.8 | Phenylalanine | 20.1 |
| | | Arginine | 69.2 | which on SDS-PAGE electrophoresis produces bands characteristic of the following molecular weights:

| | |
|---|---|
| 300,000 | 200,000 |
| 250,000 | 132,000 |
| 220,000 | 116,000 | and comparing the aggregation response of said platelets to the response of normal platelets.

10. A method of preparing a hemostatic agent comprising the steps of:

(a) extracting cleansed, homogenized, human umbilical cord tissue with dilute aqueous acid at from 0° to 5° C., (b) separate and recover a solid precipitate by centrifugation, homogenize and again extract with dilute aqueous acid at from 0° to 5° C., (c) separate solid precipitate by centrifugation and recover aqueous phase, (d) filter aqueous phase and dialyze against dilute aqueous acid at from 0° to 5° C. to produce a concentrated retentate containing the hemostatic agent; said dilute aqueous acid being at a concentration of from 0.05 to 0.1 molar.

11. A process as in claim 10 including the added steps of:

(e) recovering the solid precipitate from Step (c), (f) homogenize said precipitate and extract with dilute aqueous acid at from 0° to 5° C., (g) separate solid precipitate by centrifugation and recover aqueous phase, (h) filter aqueous phase and dialyze against dilute aqueous acid at from 0° to 5° C. to produce a concentrated retentate containing the hemostatic agent; said dilute aqueous acid being at a concentration of from 0.05 to 0.1 molar.

12. A process as in claim 11 including the added steps of:

(i) recovering solid precipitate from Step (g), (j) homogenize said precipitate and extract with dilute aqueous acid at from 0° to 5° C., (k) separate solid precipitate by centrifugation and recover aqueous phase, (l) filter aqueous phase and dialyze against dilute aqueous acid at from 0° to 5° C. to produce a concentrated retentate containing the hemostatic agent; said dilute aqueous acid being at a concentration of from 0.05 to 0.1 molar.

13. A method as in claim 12 including the added step of combining the retentates from Steps (d), (h) and (l) and subjecting the resulting combined retentates to ultracentrifugation to separate a gelled fraction containing the hemostatic agent.

14. A method as in claims 10, 11, 12 and 13 wherein the dilute acid used for extraction and dialysis is acetic acid.

* * * * *